United States Patent [19]

Ivaska et al.

[11] Patent Number: 5,001,070
[45] Date of Patent: Mar. 19, 1991

[54] METHOD FOR DETERMINING THE TOTAL CARBONATE CONTENT OF A FLUID

[75] Inventors: Ari Ivaska, Turku; Andrzej Lewenstam, Helsinki; Erkki Wanninen, Turku, all of Finland

[73] Assignee: Kone Oy, Helsinki, United Kingdom

[21] Appl. No.: 539,931

[22] Filed: Jun. 18, 1990

Related U.S. Application Data

[63] Continuation of Ser. No. 228,919, filed as PCT FI87/00134 on Oct. 2, 1987, published as WO88/02487 on Apr. 7, 1988, abandoned.

[30] Foreign Application Priority Data

Oct. 3, 1986 [FI] Finland ............................ 864006

[51] Int. Cl.⁵ .......................................... G01N 33/00
[52] U.S. Cl. .................................. 436/133; 436/68; 436/145; 436/146; 436/163; 436/174; 436/127; 204/153.21; 204/153.16
[58] Field of Search ............... 436/62, 68, 74, 81, 436/80, 84, 73, 133, 53, 145, 146, 163, 174, 52, 127; 204/1 T

[56] References Cited

U.S. PATENT DOCUMENTS

| | | | |
|---|---|---|---|
| 3,551,350 | 12/1970 | Dahms | 436/133 X |
| 4,003,705 | 1/1977 | Buzza et al. | |
| 4,092,117 | 5/1978 | Byrne | 436/73 |
| 4,149,949 | 4/1979 | Buzza et al. | |
| 4,196,056 | 4/1980 | Kumar | 204/1 T |
| 4,264,328 | 4/1981 | Marsoner | 204/1 T |
| 4,353,867 | 10/1982 | Luzzana | 422/68 |
| 4,397,957 | 8/1983 | Allison | 436/146 X |
| 4,399,225 | 8/1983 | Hansen et al. | 436/53 X |
| 4,490,234 | 12/1984 | Buzza | |
| 4,490,235 | 12/1985 | Calzi | 204/1 T |
| 4,724,216 | 2/1988 | Young et al. | 436/74 X |

FOREIGN PATENT DOCUMENTS

| | | |
|---|---|---|
| 0155162 | 9/1985 | European Pat. Off. |
| 0165607 | 12/1985 | European Pat. Off. |
| 57-203943 | 12/1982 | Japan |

OTHER PUBLICATIONS

Toren et al, Anal. Chem., vol. 29, No. 12, pp. 1854–1856, 1957.

Primary Examiner—Robert J. Hill, Jr.
Attorney, Agent, or Firm—Lowe, Price, LeBlanc, Becker & Shur

[57] ABSTRACT

An electrochemical method for determining the total carbonate content of fluids, especially biological fluids. According to the invention, using an ion-selective electrode, the concentration of certain ions dissociable from carbon acid or affecting the dissociation balance is first measured for the fluid. The fluid is then mixed with another fluid containing a reactive component that changes the ionic concentration just measured, whereupon the concentration is again measured by means of an ion-selective electrode, thus producing two different measurement results, from which the total carbonate content can be determined. The measurement preferably relates to the pH of the fluid, while metallic ions such as $Cu^{2+}$, forming a complex with hydrocarbonate ions, are used as the component to be added to alter the pH.

11 Claims, 1 Drawing Sheet

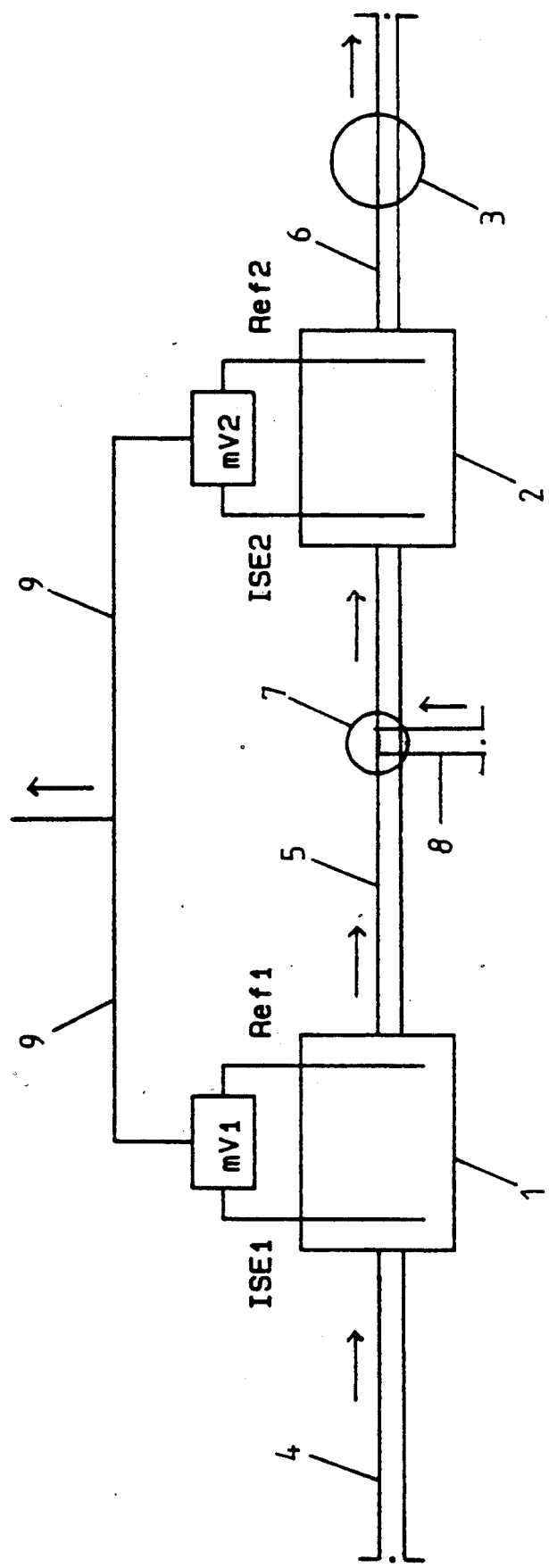

METHOD FOR DETERMINING THE TOTAL CARBONATE CONTENT OF A FLUID

This application is a Continuation application of application Ser. No. 07/228,919 filed Aug. 3, 1988 now abandoned.

The present invnetion concerns a method for determining the total carbonate content of fluids especially, biological fluids, using an ion-selective electrode for the measurement.

The biological fluids referred to are, in particular, human blood and urine, which are analyzed to determine their carbonate content for diagnostic purposes.

The methods currently use for electrochemical determination of the carbonate content in fluids are based on two fundamental solutions. One of these uses an electrode designed for sensing carbon dioxide ($CO_2$), while the other uses an electrode sensitive to carbonate ions.

The first solution is represented by U.S. Pat. No. 4,490,234, which proposes a method for determination of the total carbonate content of a fluid involving measurement of the amount of carbon dioxide in the fluid by means of an element consisting of a renewable electrolyte disposed between a gas-permeable membrane and an ion-selective electrode. In this method, the sample fluid is premixed with an acid to release carbon dioxide. The gassed sample is then pumped toward the said element, while at the same time the electrolyte is also circulated by pumping. When the sample reaches the element, the pumping is stopped. The gas then diffuses through the membrane into the electrolyte solution, and the change occurring in the latter is measured by the ion-selective electrode and translated into a total carbonate content value. The disadvantages of this method are the need for a two-channel fluid pumping system and the use of a gas-permeable membrane, which may be blocked with time by constituents in the sample, such as proteins.

The second solution is represented by U.S. Pat. No. 4,196,056, which involves the use of an in-selective carbonate electrode. As described in the patent publication, the sample is premixed with a pH buffer solution containing a mercury/EDTA complex. This has the main effect of producing carbonate ions, which are then sensed by the electrode. The drawbacks of this method are related in the first place to the imperfections of the ion-selective electrode, such as instability of the signal, long response time, short durability and sensitivity to other ions and substances.

The object of the present invention is to provide a new method for determining the total carbonate content of a fluid in a simple, fast and accurate manner without the above-mentioned disadvantages of existing methods. The invention is characterized in that the fluid is first subjected to a measurement, using an ion-selective electrode, of the concentration of certain ions dissociable from carbon acid or affecting the dissociation balance, that the fluid is then mixed with another fluid containing a reactive component that changes the concentration of said ions thus measured, and that after the mixing the ionic concentration is again measured by means of an ion-selective electrode, thus producing two different measurement results, from which the total carbonate content can be determined.

The method of the invention allows concentration measurements without generation of gases. The advantage of this is that no accurate pressure control and no dialysis membrane is necessary. This obviates the danger of membrane blockages, which present the worst problems with the existing methods.

Further, an essential feature in the method of the invention is that the determination of the carbonate content is based on the chemical laws governing the balance of different ions in a fluid, i.e. the method has an exact scientific foundation ensuring reliable results.

An embodiment of the method of the invention is characterized in that it uses fluid containing ions of a metal, e.g. $Cu^{2+}$, $Pb^{2+}$, $Cd^{2+}$, $Mn^{2+}$ or $Zn^{2+}$, which form a complex with carbonate or hydrocarbonate ions. Copper ions are particularly suitable, since reagents containing copper ions are stable and inexpensive. A copper ion reacts with a hydrocarbonate ion as follows:

$$Cu^{2+} + 2\ HCO_3^- \rightarrow CuCO_3 + H_2CO_3$$

A similar reaction also occurs with the other metallic ions mentioned above. Thus in all cases the reaction involves ions only and is very fast.

Another embodiment of the method of the invention is characterized in that the electrochemical concentration measurement relates to hydrogen ions, in other words, that the pH of the fluid containing carbonate is measured. The measurement can be performed using a glass electrode, which, unlike the electrodes normally used for testing biological fluids, is fast, accurate and free of interference in operation.

In an advantageous embodiment of the method of the invention, the carbonate content is determined by using a device consisting of two cascade-connected measuring cells, the fluid containing carbonate being stopped in the first cell, where the concentration of given ions, such as hydrogen ions, is measured with an ion-selective electrode incorporated in the cell, from where the fluid is then pumped into the second cell, where it is stopped and the ionic concentration is again measured with an ion-selective electrode incorporated in the cell, the fluid being mixed between the two cells with another fluid containing a component, e.g. metallic ions forming a complex with carbonate or hydrocarbonate ions, altering the said ionic concentration. The necessary fluid motion can be achieved with a single one-channel peristaltic pump, and in general the required equipment is simple in construction.

The second fluid to be added to the fluid under carbonate measurement preferably contains metallic ions such as copper, lead, cadmium, manganese or zinc ions in the form of a dissolved salt, e.g. a nitrate with a concentration in the range of $1 \times 10^{-3}M - 2.5 \times 10^{-2}M$, said ions forming a complex with the carrier electrolyte, e.g. potassium nitrate, which may have a concentration in the range of 0.15M-1M, and a substance inhibiting secondary reactions of the metallic ions, e.g. hydrogen peroxide or $Fe^{3+}$ ions, preferably in a concentration of $1 \times 10^{-4} - 1 \times 10^{-1}M$.

BRIEF DESCRIPTION OF THE DRAWING

In the following, the invention is described in greater detail by the aid of an example, reference being made to the drawing attached, showing a diagram of set of equipment designed for applying the method of the invention.

The equipment shown in the drawing comprises a measuring cell 1, which is provided with an ion-selective electrode ISE1 and a reference electrode REF1, the potential difference between these being measured with a potentiometer mV1, a second measuring cell 2, which is provided with an ion-selective electrode ISE2 and a reference electrode REF2, the potential difference between these being measured with a potentiometer mV2, and tubes 4, 5, 6, connected to a pump 3 and serving to pass the fluid sample through the measuring cells. The tube 5 between the two cells is provided with a valve 7 communicating with a branch tube 8, through which a second fluid can be added to the fluid flowing in the tube 5 between the cells. The potential differences measured in the two cells are transmitted to a computer or a similar calculating device via the potentiometer output conductors, identified with reference number 8 in the drawing.

In the most advantageous application of the invention, the fluid sample, e.g. a blood sample, for which the total carbonate content is to be found out, is passed via the tubes 4, 5, 6 through the measuring cells 1 and 2, and a potentiometric pH measurement is performed in both cells, using glass electrodes sensitive to hydrogen ions. For each measurement, the sample is stopped in the cell. Between the cells, a second fluid, introduced via the tube 8, is added to the sample. This second fluid is preferably a reagent, e.g. a mild copper nitrate solution, containing divalent copper ions, potassium nitrate as a carrier electrolyte and hydrogen peroxide to inhibit secondary reactions of the copper ions. The copper ions react with hydrocarbonate ions contained in the sample in the manner expressed by the equation on page 3, thus consuming hydrocarbonate ions and producing carbonic acid, thereby altering the pH of the sample. Therefore, the pH measurement in the second cell 2 yields a result different from that obtained in the first cell 1, and the total carbonate content of the sample can be calculated from these two results.

The total carbonate content CL is calculated from the formula:

$$CL = Q \left( \frac{1 + 2[H^+]_2 K_{II}}{\frac{[H^+]_2 K_{II}}{\alpha_{HL(H)_1}} - \frac{1}{\alpha_{H_2L(H)_1}}} \right)$$

where Q is a constant determined by the size of the sample and the quantity and concentration of the reagent employed, and where $$\alpha_{HL}(H)_1 = \frac{1}{K_I [H^+]_1} + 1 + K_{II}[H^+]_1$$

$$\alpha_{H_2L}(H)_1 = \frac{1}{K_I K_{II} [H^+]_1^2} + \frac{1}{K_{II}[H^+]_1} + 1$$

$$K_I = \frac{[HCO_3^-]}{[CO_3^{2-}][H^+]}$$

$$K_{II} = \frac{[H_2CO_3]}{[HCO_3^-][H^+]}$$

The subscripts "1" and "2" in the formulas above refer to the pH measurements in cells 1 and 2 respectively. The constants Q and $K_I$ are calculated beforehand from the formula (I) and using two buffer solutions with a known $C_L$ value. Once the constants have been determined, the formula can be used to calculate the total carbonate content $C_L$.

It is obvious to a person skilled in the art that the embodiments of the invention are not restricted to the example described above, but that they may instead be varied in the scope of the claims presented below. Thus it is possible that instead of copper ions, other ions forming a complex with carbonate or hydrocarbonate ions are used, e.g. $Pb^{2+}$, $Cd^{2+}$, $Mn^{2+}$ ions, or that instead of the pH, the concentration of hydrocarbonate or carbonate ions is measured in the cells. Further, it is possible to interchange the sample containing carbonate and the reagent, such as the mentioned reagent containing copper ions, so that the reagent is first brought into the measuring cell 1, where its copper content is measured with a suitable copper-selective electrode, whereupon the sample containing carbonate is added to the reagent via the tube 8 and the copper content of the mixture thus obtained is measured in the second cell 2 with a copper-selective electrode. The total carbonate content of the sample can then be calculated from the measurement results obtained.

We claim:

1. A method for determining the total carbonate content in a biological fluid consisting essentially of a first step of measuring the pH of the biological fluid by means of a pH-electrode; a second step of mixing the biological fluid with a metal ion-containing reagent which forms a complex with carbonate or hydrocarbonate ions, thereby changing the pH of the biological fluid; and a third step of again measuring the pH of the biological fluid by means of a pH-electrode, thereby producing two different measurement results from which the total carbonate content of the biological fluid can be determined.

2. A method as claimed in claim 1, wherein the metal ion is selected from the group consisting of $Cu^{2+}$, $Pb^{2+}$, $Mn^{2+}$ and $Zn^{2+}$ ions.

3. A method as claimed in claim 1, wherein the carbonate content is determined using a device comprising two cascade-connected measuring cells, the biological fluid being placed in the first cell and the pH of the biological fluid being measured with a pH-selective electrode incorporated in the cell, and the biological fluid then being pumped into the second cell, the fluid being mixed between the two cells with said metal ion-containing reagent, and the pH of the biological fluid being measured in said second cell with a pH-electrode incorporated in the second cell.

4. A method as claimed in claim 1, wherein said metal ion-containing reagent also contains a carrier electrolyte and a substance inhibiting secondary reactions of said metal ion, said metal ion being in the form of a dissolved salt which forms a complex with said carrier electrolyte.

5. A method as claimed in claim 4, wherein the carrier electrolyte is potassium nitrate and the substance inhibiting secondary reactions is selected from the group consisting of hydrogen peroxide and $Fe^{3+}$ ions.

6. A method for determining the total carbonate content in a biological fluid, which method comprises a first step of measuring the concentration of carbonate or hydrocarbonate ions contained in the biological fluid by means of a carbonate ion-selective electrode: a second step of mixing the biological fluid with a metal ion-containing reagent which forms a complex with carbonate or hydrocarbonate ions, thereby changing the concentration of the carbonate or hydrocarbonate ions measured in the first step; and a third step of again measuring the carbonate or hydrocarbonate ion concentration by means of a carbonate ion-selective electrode, thereby producing two different measurement results from which the total carbonate content of the biological fluid can be determined.

7. A method for determining the total carbonate content in a biological fluid, which method comprises a first step of measuring the concentration of metal ions contained in a metal ion-containing reagent, said measurement being carried out by means of an appropriate metal ion-selective electrode; a second step of mixing the metal ion-containing reagent with the biological fluid, the metal ions forming a complex with carbonate or hydrocarbonate ions in the biological fluid; and a third step of measuring the metal ion concentration of the resulting mixture by means of a metal ion-selective electrode, thereby producing two different measurement results from which the total carbonate content of the biological fluid can be determined.

8. A method as claimed in claim 7, wherein the metal ion is selected from the group consisting of $Cu^{2+}$, $Pb^{2+}$, $Cd^{2+}$, $Mn^{2+}$ and $Zn^{2+}$ ions.

9. A method as claimed in claim 7, wherein the carbonate content is determined using a device comprising two cascade-connected measuring cells, the metal ion-containing reagent being placed in the first cell and the concentration of the metal ion in the metal ion-containing reagent being measured with an appropriate metal ion-selective electrode incorporated in the cell, and the metal ion-containing reagent then being pumped into the second cell, the reagent being mixed between the two cells with said biological fluid, and the metal ion concentration of the resulting mixture being measured in said second cell with an appropriate metal ion-selective electrode incorporated in the second cell.

10. A method as claimed in claim 7, wherein said metal ion-containing reagent also contains a carrier electrolyte and a substance inhibiting secondary reactions of said metal ion, said metal ion being in the form of a dissolved salt which forms a complex with said carrier electrolyte.

11. A method as claimed in claim 10, wherein the carrier electrolyte is potassium nitrate and the substance inhibiting secondary reactions is selected from the group consisting of hydrogen peroxide and $Fe^{3+}$ ions.

* * * * *

UNITED STATES PATENT AND TRADEMARK OFFICE
CERTIFICATE OF CORRECTION

PATENT NO. : 5,001,070
DATED : March 19, 1991
INVENTOR(S) : Ari IVASKA et al.

It is certified that error appears in the above-identified patent and that said Letters Patent is hereby corrected as shown below:

On the title page, please correct item [73] as follows:

[73] Assignee: Kone Oy, Helsinki, Finland

Signed and Sealed this

Twenty-fifth Day of May, 1993

Attest:

MICHAEL K. KIRK

Attesting Officer

Acting Commissioner of Patents and Trademarks